United States Patent [19]

Müller et al.

[11] Patent Number: 5,296,237

[45] Date of Patent: Mar. 22, 1994

[54] WATER-SOLUBLE PHARMACEUTICAL METALLOCENE-COMPLEX COMPOSITION

[75] Inventors: Bernd W. Müller, Flintbek; Rainer Müller; Stefan Lucks, both of Kiel; Wilfried Mohr, Hamburg, all of Fed. Rep. of Germany

[73] Assignee: medac Gesellschaft fur klinische Spzeialpraparate mbH, Hamburg, Fed. Rep. of Germany

[21] Appl. No.: 810,449

[22] Filed: Dec. 19, 1991

Related U.S. Application Data

[63] Continuation of Ser. No. 552,749, Jul. 16, 1990, abandoned.

[30] Foreign Application Priority Data

Jul. 14, 1989 [DE] Fed. Rep. of Germany ....... 3923270

[51] Int. Cl.$^5$ .............................................. A61K 31/28
[52] U.S. Cl. .................................... 424/489; 424/617; 424/646
[58] Field of Search .............. 514/492; 424/617, 484, 424/646, 617, 489

[56] References Cited

U.S. PATENT DOCUMENTS

| | | | |
|---|---|---|---|
| 4,296,030 | 10/1981 | Lang, Jr. et al. | 424/530 |
| 4,578,401 | 3/1986 | Keller et al. | 514/49 |
| 4,608,387 | 8/1986 | Kopf et al. | 514/492 |
| 4,608,387 | 8/1986 | Kopf | 514/492 |
| 4,767,874 | 9/1988 | Shima et al. | 556/137 |
| 4,851,430 | 7/1989 | Kopf-Maier et al. | 514/492 |
| 4,889,715 | 12/1989 | Sawai et al. | 424/78.05 |
| 5,002,969 | 3/1991 | Kopf-Maier et al. | 514/492 |

FOREIGN PATENT DOCUMENTS

0202673  11/1986  European Pat. Off. .
2-69491   3/1990  Japan .

*Primary Examiner*—Thurman K Page
*Assistant Examiner*—Peter F. Kulkosky
*Attorney, Agent, or Firm*—Nixon & Vanderhye

[57] ABSTRACT

A water-soluble metallocene-complex composition which can be used as a cytostatic is described, which can be obtained by mixing a metallocene complex, a polyol, water and optionally additives, whereby glycols, sugar alcohols and carbohydrates are primarily used as the polyols.

10 Claims, No Drawings

WATER-SOLUBLE PHARMACEUTICAL METALLOCENE-COMPLEX COMPOSITION

This is a continuation of application Ser. No. 07/552,749, filed Jul. 16, 1990, now abandoned.

The invention relates to a water-soluble pharmaceutical metallocene-complex composition which can be used as a cytostatic in cancer-therapy.

The use of metallocene-complexes as cytostatica is known from DE-C-29 23 334 and DE-C-35 18 447. The complexes are very poorly water-soluble due to the lipophilic cyclopentadienyl groups and in addition have proved relatively unstable in aqueous solution so that parenteral administration, e.g. in the form of a solution for injection, has not been possible.

In Dokl. Akad. Nauk SSR 266, 883 (1982) water-soluble vanadocene acylates are described which are produced by the reaction of vanadocene with hydroxypropane tricarboxylic acid. This method is restricted to these special anions.

DE-A-29 23 334 describes the use of dimethyl sulphoxide as solubilizer for the titanocenes. The dimethyl sulphoxide is disadvantageous on the grounds of its own pharmacodynamic effect and its embryo-toxicity.

It is also known from a paper by K. Doppert, J. Organomet. Chem. 319, 351 (1987) that titanocene complexes in aqueous solutions are degraded through hydrolysis to insoluble polymers. It therefore appeared impossible to convert metallocene complexes, particularly titanocene complexes, into a water-soluble form from which can be produced injection-solutions with therapeutic concentrations of the metallocene complex which have sufficient stability for parenteral administration.

The basic object of the invention is to make available a physiologically acceptable water-soluble, pharmaceutical metal-locene-complex composition which is sufficiently stable in the form of an aqueous solution with therapeutic concentrations of the metallocene complex for administration by parenteral route, and a process for the production of this composition. Such solutions are of special interest as a cytostatic in cancer-therapy.

This problem is surprisingly solved by the metallocene-complex composition of the invention according to claims 1 to 8 and the process for its production according to claims 9 to 11.

The water-soluble, pharmaceutical metallocene-complex composition according to the invention is characterized in that it can be obtained by mixing together a metallocene complex, a polyol, water and optionally additives, and then removing the water from the mixture.

The composition according to the invention can preferably be obtained by mixing
  0.01 to 2 % by weight of metallocene complex,
  0.1 to 20 % by weight of polyol,
  58 to 99.89 % by weight of water and
  optionally 0 to 20 % by weight of additives.

The metallocene-complex composition according to the invention can be obtained in the most preferred way by mixing
  0.02 to 0.4 % by weight of metallocene-complex,
  0.5 to 6.0 % by weight of polyol,
  91.6 to 99.48 % by weight of water and
  0 to 3.0 % by weight of additives.

Useful metallocene-complexes are compounds of the general formula $(Cp)_2M^nX_{n-2}$, in which Cp represents the cyclopentadienyl anion, M a transition metal of valency n, and X a mono- or polyvalent anion. Preferably the complexes correspond to general formula $Cp_2M^{IV}X_2$. is preferably a halide, especially a chloride, but may also be another anion.

As metallocene complexes, the following are preferably used: vanadocene, hafnocene, zirkonocene, molybdenocene, tantalocene complexes and/or mixtures thereof; particularly preferred are titanocene complexes, particularly titanocene dichloride. The term metallocene complexes is understood to include both metallocene compounds which have no substitution on the two cyclopentadiene rings and those which are substituted on at least one of the cyclopentadiene rings.

As polyols, the following are preferably used: glycols, sugar alcohols, carbohydrates or mixtures thereof, and particularly preferably glycerol, 1,2-propylene glycol, 1,5-pentanediol, polyethylene glycols, block-copolymers of propylene glycol and ethylene glycol, pentaerythritol, glucose, fructose (saccharose), lactose or mixtures thereof and most particularly preferred sucrose, lactose, glucose, mannitol, sorbitol and mixtures thereof. Most useful are polyols having a glass transition temperature $T_g$ in the range of about $-30°$ C. to $-50°$ C.

As additives sodium chloride can be used as an isotonicity-regulator, preferably in quantities of about 0.9 % by weight.

In the preparation of the compositions according to the invention, metallocene complex, polyol, water and the optionally used additives are mixed and then the water in this mixture is removed, preferably by means of freeze-drying. For accelerated dissolution or dispersion of the metallocene complex in the aqueous solution, the mixture is preferably subjected to ultrasonic waves. Optionally the dissolution may also be carried out under heating. For a large-scale industrial production of the composition according to the invention, instead of ultrasound treatment, cosolvents such as, for example, dimethyl sulphoxide and tetrahydrofuran, can be used, preferably in concentrations of 0.5 to 10% by weight. They accelerate the dissolution or the dispersion of the metallocene complex in the aqueous solution. When using cosolvents it must, however, be taken into consideration that the eutectic temperature of the mixture and therefore the transition temperature and also the parameters of the freeze-drying process are changed. The cosolvents are removed together with the water by the freeze-drying, so that the metallocene-complex composition according to the invention is obtained as dry substance. It is completely re-soluble on addition of water and forms a clear solution sufficiently stable for a parenteral administration. The metallocene complex is contained therein preferably in concentrations of 0.05 to 5 mg/ml $H_2O$. The increased stability of the aqueous solution of the composition according to the invention compared with the aqueous solution of metallocene complexes is indicated by the clouding due to the formation of di- and oligomers appearing considerably later. A water-soluble pharmaceutical metallocene-complex composition is therefore made available which is sufficiently stable in the form of its aqueous solution containing therapeutic concentrations of metallocene complex to be conveniently applied by parenteral route as a cytostatic in cancer-therapy.

The invention is illustrated in more detail in the following examples.

EXAMPLE 1

20.0 mg titanocene dichloride
90.0 mg sodium chloride
100.0 mg mannitol
10.0 ml water (aqua pro injectione)

The components indicated above were mixed, the mixture was exposed to ultrasonic waves for approx. 1 hour, filtered through a 0.45 μm membrane filter and frozen at −50° C. in an injection bottle. After the subsequent freeze-drying at −35° C., the lyophilizate could be completely dissolved in water forming a stable, clear solution. The concentration of the active ingredient in this solution was 2 mg of active ingredient per 1 ml of solution.

EXAMPLE 2

10 mg titanocene dichloride
45 mg sodium chloride
255 mg sorbitol
5 ml water (aqua pro injectione)

Preparation was as described under Example 1. The solution obtained by dissolving the lyophilizate in water contained the active ingredient in a concentration of 2 mg/ml.

EXAMPLE 3

10 mg titanocene dichloride
255 mg sorbitol
5 ml water (aqua pro injectione)

Preparation was as described under Example 1. The lyophilizate obtained by the freeze-drying produced a clear, isotonic solution with 5 ml of water with 2 mg of active ingredient per ml solution.

EXAMPLE 4

10 mg titanocene dichloride
100 mg dimethyl sulphoxide
255 mg sorbitol
5 ml water (aqua pro injectione)

After mixing and dissolving the above components, the solution obtained was filtered through a 0.45 μm membrane-filter, frozen at −70° C. and then freeze-dried. In addition to the water the cosolvent dimethyl sulphoxide was also removed thereby. The lyophilizate obtained was completely soluble in 2 ml of water and formed an isotonic, stable solution with an active ingredient content of 2 mg/ml.

EXAMPLE 5

Solutions of the following composition were prepared:

2 mg titanocene dichloride
51 mg polyol
10 ml water (aqua pro injectione)

The following were used as polyol:
A. sucrose
B. lactose
C. glucose

The following conditions were employed for the freeze drying:

|   | temperature | pressure |
| --- | --- | --- |
| A | −37° C. | $<2 \cdot 10^{-1}$ mbar |
| B | −35° C. | $<2.5 \cdot 10^{-1}$ mbar |
| C | −50° C. | $<3.9 \cdot 10^{-2}$ mbar |

After removal of most of the water which was achieved after several hours the vacuum was gradually reduced and simultaneously the temperature raised by increments of 7° C. up to 20° C.; if necessary for the complete drying the temperature may be raised up to 40° C. Essentially water-free lyophilisates were obtained which could easily be dissolved in water.

EXAMPLE 6

Example 3 was repeated using the following metallocene complex compounds

A. 10 mg Zirconocene dichloride (white crystalline powder)
B. 10 mg hafnocene dichloride (white crystalline powder having a certain caking tendency)
C. 10 mg molybdenocene dichloride (black-brown powder of small particle size)
D. 10 mg vanadocene dichloride (dark green crystalline powder)
E. 10 mg vanadocene dichloride +10 mg ascorbic acid 5 ml of an isotonic sorbitol solution (corresponding to 255 mg sorbitol in the lyophilisate) were added to samples A to E.

Sample A was dissolved in the sorbitol solution at room temperature after some shaking and a colorless solution was obtained.

Sample B dissolved more slowly, the dissolution was supported by an ultrasonic sound treatment. The compound yielded a clear colorless solution.

Sample C dissolved rather slowly, an ultrasonic treatment increased the dissolution rate considerably. The dark powder yielded at first a dirty brown suspension which was converted into a dark green clear solution after a short time (3 to 4 minutes).

Samples D and E showed a similar solubility behavior as titanocene dichloride. An ultrasonic treatment was used to break up the lumps of compound. Heating assisted considerably in dissolving the complex. The vanadocene dichloride dissolved in the sorbitol solution to give a clear dark green solution.

After dissolution the sample vials were frozen in a deepfreezer at −18° C. and then cooled down in the freeze dryer to −35° C. for 24 hours whereafter the drying operation was carried on for four days.

No complications occurred during the freeze drying of samples A and B. In both cases a fluffy white lyophilisate was formed.

When drying sample C (molydenocene dichloride) the color changed from dark green to beige. A fluffy lyophilisate was formed.

When freeze drying sample E (with ascorbic acid) some melting occurred at the surface at a temperature of −35° C. The drying operation was nevertheless continued. The lyophilisate obtained from samples D and E showed a green color, the molten areas appeared somewhat darker.

The lyophilisates of samples A and B showed excellent solubility. After addition of water and short shaking (maximum 30 seconds) a clear colorless solution was obtained. The lyophilisate of sample C had to be shaken for about 5 minutes with water in order to obtain a clear solution. The beige colored lyophilisate was slowly converted into an olive green solution. A freshly prepared comparative solution of molybdenocene dichloride showed the identical color.

The lyophilisate of the vandocene dichloride showed a similar dissolution rate as titanocene dichloride, independently of the absence or presence of ascorbic acid. After addition of water shaking for about 2 minutes was necessary in order to obtain a clear dark green solution.

The solutions formed from each of the lyophilisates proved to be stable and useful for parenteral administration.

We claim:

1. A water-soluble lyophilized powdered pharmaceutical composition consisting essentially of a metallocene complex of the formula $(Cp)_2M^nX_{n-2}$ where Cp represents the cyclopentadienyl anion, M a transition metal of valency n, and X a mono- or polyvalent anion and a polyol selected from the group consisting of glycerol, 1,2-propylene glycol, 1,5-pentanediol, polyethylene glycol, a block copolymer of propylene glycol and ethylene glycol, pentaerythritol, sorbitol, mannitol, glucose, fructose, sucrose, lactose and mixtures thereof, which when re-solubilized in water forms a solution.

2. A water soluble, lyophilized powdered pharmaceutical composition prepared from an aqueous solution of 0.01 to 2% by weight of a metallocene complex of the formula $(Cp)_2M^nX_{n-2}$ where Cp represents the cyclopentadienyl anion, M is a transition metal of valency n, and X a mono- or polyvalent anion, 58 to 99.89% by weight water, 0.1 to 20% by weight of a polyol selected from the group consisting of glycerol, 1,2-propylene glycol, 1,5-pentanediol, polyethylene glycol, a block copolymer of propylene glycol and ethylene glycol, pentaerythritol, sorbitol, mannitol, glucose, fructose, sucrose, lactose and mixtures thereof, from which solution the water has been removed.

3. The water soluble, lyophilized powdered pharmaceutical composition of claim 2, wherein said aqueous solution, prior to lyophilization, also contained up to 20% by weigh of an isotonicity regulator.

4. The water soluble lyophilized powdered pharmaceutical composition of claim 3 wherein said aqueous solution, prior to lyophilization, contained 0.02 to 0.4% by weight of a metallocene complex, 0.5 to 6.0% by weight of said polyol, 91.6 to 99.48% by weight of water and 0 to 3.0% by weight of an isotonicity regulator.

5. The water-soluble, lyophilized powdered pharmaceutical composition of claim 1 or 3, wherein the metallocene complex is a complex of titanocene, tantalocene, hafnocene, zirconocene, molybdenocene, vanadocene, or mixtures thereof.

6. The water-soluble, lyophilized powdered pharmaceutical composition of claim 5 wherein titanocene dichloride is the metallocene complex.

7. The water-soluble, lyophilized powdered pharmaceutical composition of claim 1 wherein sodium chloride is the isotonicity regulator.

8. A stabilized solution for parenteral administration containing a therapeutically effective concentration of a water-soluble metallocene complex which is prepared by dissolving the water-soluble lyophilized powder of claim 1 or 2 in an aqueous medium for parenteral administration wherein the stability of said solution is increased as compared to a non-polyol containing aqueous solution of said metallocene complex.

9. The stabilized solution of claim 8 containing from 0.05 to 0.5 mg/ml of the metallocene complex.

10. A method of treating a patient having a tumor comprising parenterally administering to the patient a cytostatically effective amount of the composition of claim 8.

* * * * *